Figure 1:
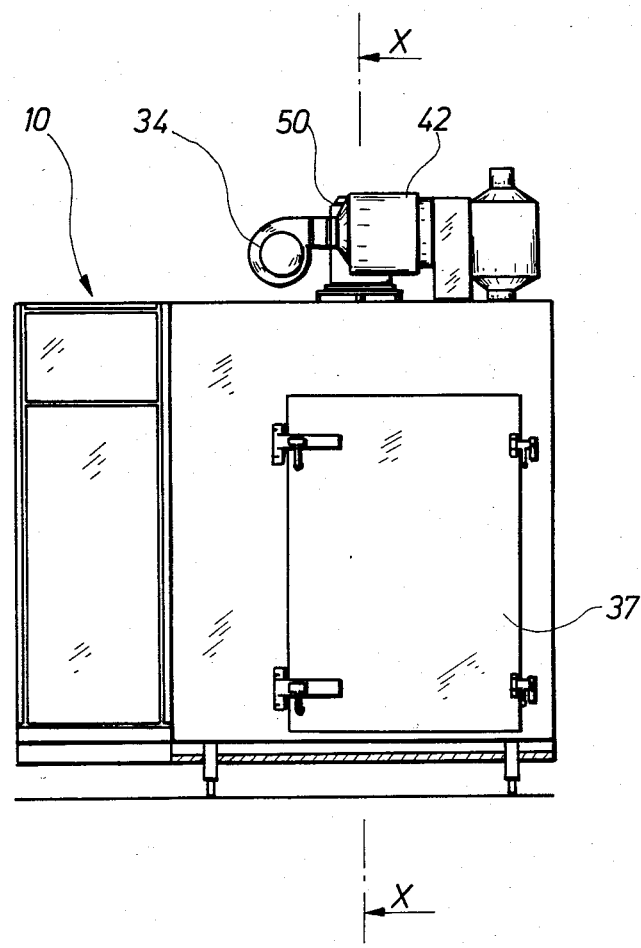

United States Patent [19]

Vestergaard

[11] Patent Number: 4,498,678
[45] Date of Patent: Feb. 12, 1985

[54] SHAFT SEAL

[75] Inventor: Alex D. Vestergaard, Kastrup, Denmark

[73] Assignee: Ingeniørfirmaet Lytzen KS, Herley, Denmark

[21] Appl. No.: 470,184

[22] Filed: Feb. 28, 1983

[30] Foreign Application Priority Data

Mar. 3, 1982 [DK] Denmark .............................. 913/82

[51] Int. Cl.³ .............................................. F16J 15/40
[52] U.S. Cl. ............................................ 277/3; 277/36
[58] Field of Search ...................... 34/195, 196; 277/3, 277/36

[56] References Cited

U.S. PATENT DOCUMENTS

| 1,956,366 | 4/1934 | Vedovell | 277/36 |
| 3,083,974 | 4/1963 | De Moude | 277/36 |
| 3,180,134 | 4/1965 | Wadlington | 277/3 |
| 3,181,873 | 5/1965 | Reed | 277/3 |
| 4,087,097 | 5/1978 | Bossens et al. | 277/3 |

Primary Examiner—Robert I. Smith
Attorney, Agent, or Firm—Fitch, Even, Tabin & Flannery

[57] ABSTRACT

In a sterilizing oven filtered air is circulated by a circulator situated within the oven and driven by an electric motor through a shaft, said motor being situated outside the oven. Since the air within the sterilizing oven must have a very low content of particles compared to common atmospheric air, it must not be possible for air to penetrate from the outside through the extension of the shaft. The shaft is therefore received in two spring-loaded gaskets in a sealing chamber which is supplied with filtered air at a low overpressure through a connection to a pump.

9 Claims, 3 Drawing Figures

SHAFT SEAL

The invention relates to a shaft seal about a rotating shaft extending through an opening in a plate wall such as an oven shell, which separates an impure and a pure chamber, e.g. a non-sterile chamber (a working chamber) and a sterile chamber (a sterilizing oven), whereby these chambers contain their respective qualities of one and the same medium such as atmospheric air, and whereby at least one quality (the sterile quality) must not be mixed with the other quality.

Danish patent specification No. 140,859 discloses a seal ensuring a mutual separation of two media. In connection with such a seal, a gasket of a resilient material is placed about the rotating shaft, and a pressure medium is provided between the shaft and the gasket. This pressure medium is capable of oozing out to both sides through the resulting slot-shaped space, the size of which is determined by the force that the pressure medium is subjected to by said portion and by the pressure in the medium fed to the separating surface. Such a seal is, however, not particularly heat-resisting since the resilient material is gradually broken down if it is subjected to the strong heating which for instance may take place at the mounting on a sterilizing oven.

A sterilizing oven is especially used for sterilizing hospital equipment. Beyond killing bacteria and the like during the heating in the oven, filtered air is used for removing foreign particles from the articles that are sterilized. Sterilizing ovens are divided into classes depending on the degree of purity reached by the filtered air. Ovens in class 100 must for instance contain less than 100 foreign particles in one cubic foot according to U.S. federal standard 209a. Such a content is extremely low compared to the content of particles in common atmospheric air. Therefore such an oven presents great demands to the seal of all connections.

In the sterilizing oven used together with the shaft seal according to the invention, all the connections in the interior oven shell are solidly welded, and the oven doors are mounted with double sealing strips and a particular tightening mechanism. The filtered air in the oven is circulated by a circulator driven by an electric motor through a shaft. Since the motor cannot stand up to be situated within the oven chamber, it is placed on top of the oven and the shaft extends through the upper oven shell. This shaft lead-in presents a particular sealing problem.

The object of the present invention is to provide a shaft seal unusual by the fact that it must operate in 100% dry ambience, completely without any kind of lubrication, and with a life of about 10 years without examination. During these 10 years it must be capable of standing up to frequent heatings to several hundred degrees (usually up to 300° C., in other cases and with another selection of material up to at least 600° C.) and subsequent coolings without ever releasing wear particles, at the same time as it prevents air coming from the outside from penetrating into a pure chamber.

These extreme requirements are due to the fact that the shaft seal must be operative in connection with a sterilizing oven.

Known packings for through-going shafts comprise bearing surfaces with a rotating and a stationary part situated close to each other and sealing by being in physical contact and by squeezing towards each other. By such packings, wear particles disengage unavoidably themselves, which cannot be tolerated in connection with a sterilizing oven.

Danish patent specification No. 56,333 deals thus with a shaft packing form machines comprising an oil pressure lubrication system and a shaft carried airtightly out of its crankcase in the machine through a bearing and a stuffing box situated in connection therewith. This packing provides a reduction of the wear of the surface of a packing by the packing forming part of the oil pressure lubrication system. The wear is thus reduced, but in no way removed, and the pressure packing lubricated with oil is quite unsuitable for the present purpuse.

The shaft seal according to the present invention is characterized by the shaft being loosely received by a circumferential slip in two spring-loaded and displaceable gaskets co-operating with the walls of a sealing chamber about the lead-in of the shaft through the plate wall, said sealing chamber communicating with a means such as a filter for treating the medium in question, whereby the means in turn is connected with the delivery side of a pump ending outside the pure chamber, preferably in the impure chamber, on the suction side.

In this manner the shaft seal operates without an actual physical contact between the rotating shaft and the stationary parts, viz. the plate wall, the sealing chamber, and the gaskets. As a result, wear particles do not arise. "The seal" is consequently not an actual seal, but a sort of "lock", whereby the lock between the impure air and the sterile air is maintained by means of a superatmospheric pressure within the sealing chamber between the two different chambers.

The sealing chamber may according to the invention advantageously be situated on the outside of the plate wall and be defined by said plate wall as well as by a preferably circular plate portion pressed outwards, e.g. of stainless steel, said plate portion being shaped with a circular surface at a distance from and parallel to the plate wall, whereby the circular surface continues into and is defined by a short circular-cylindrical surface in turn continuing into a surface extending radially outwards from the cylindrical surface parallel to the plate wall and being air-tightly secured thereto, e.g. screwed thereon by means of intermediary gaskets.

The spring-loaded gaskets are according to the invention preferably made of a heat-resisting material, e.g. teflon, and each gasket is shaped with a central, circular hole exactly so great that the shaft can be received in said hole in an easily sliding fitting. As a result, an almost complete seal between the gaskets and the shaft is obtained.

It is according to the invention preferred that the spring-loaded gaskets abut their respective walls in the sealing chamber and are mutually spaced by a compression spring. As a result, a good seal between each gasket and the sealing chamber is obtained. Thereby only quite small amounts of air need to be supplied in order to introduce a superatmospheric pressure within the sealing chamber.

The compression spring is according to the invention preferably a spiral spring or a conical spiral spring.

The invention is especially directed to the case where the media mentioned in the introduction are common atmospheric air and filtered, sterilized air, respectively, having a more specified max. content of particles, e.g. of the magnitude 100 particles per cubic foot corresponding to class 100 for sterilizing ovens. The medium fed to the shaft seal through the nozzle of the sealing chamber may then suitably be purified, filtered air fed at an overpressure corresponding to a water column of about 5 mm.

Figure 2:
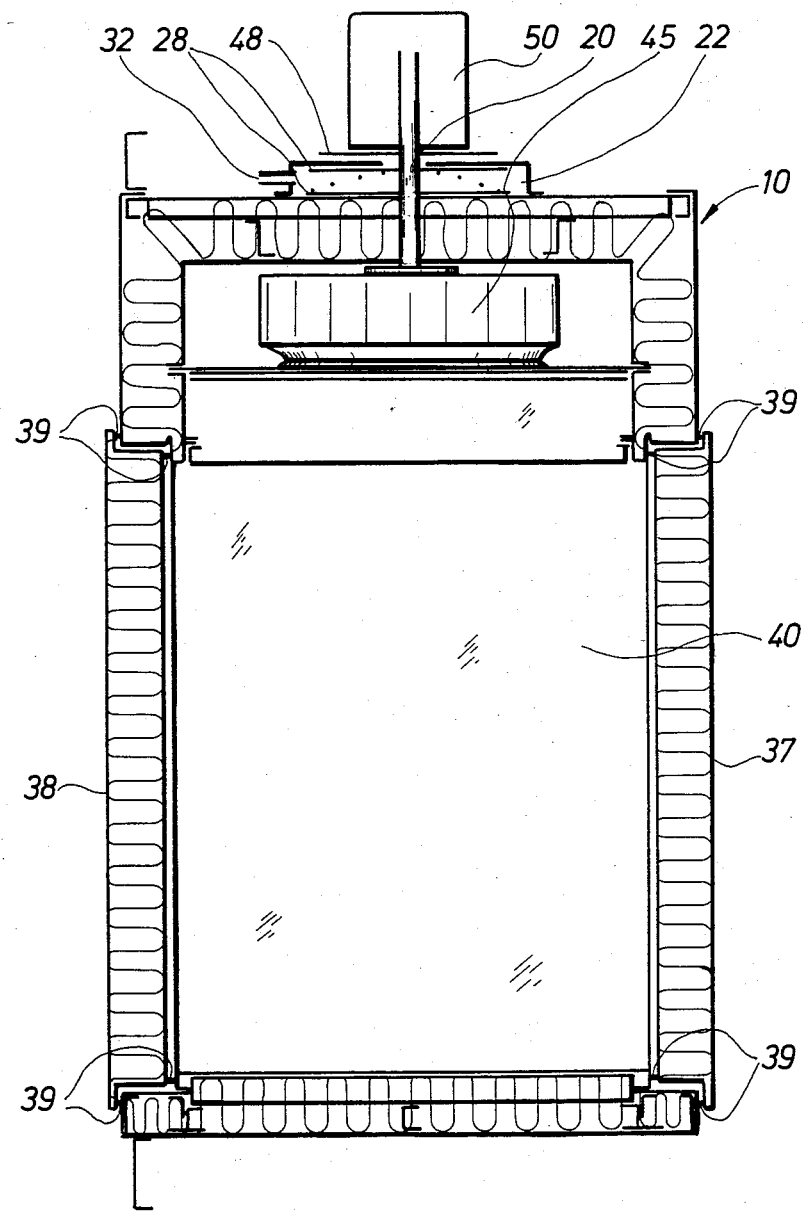
Figure 3:
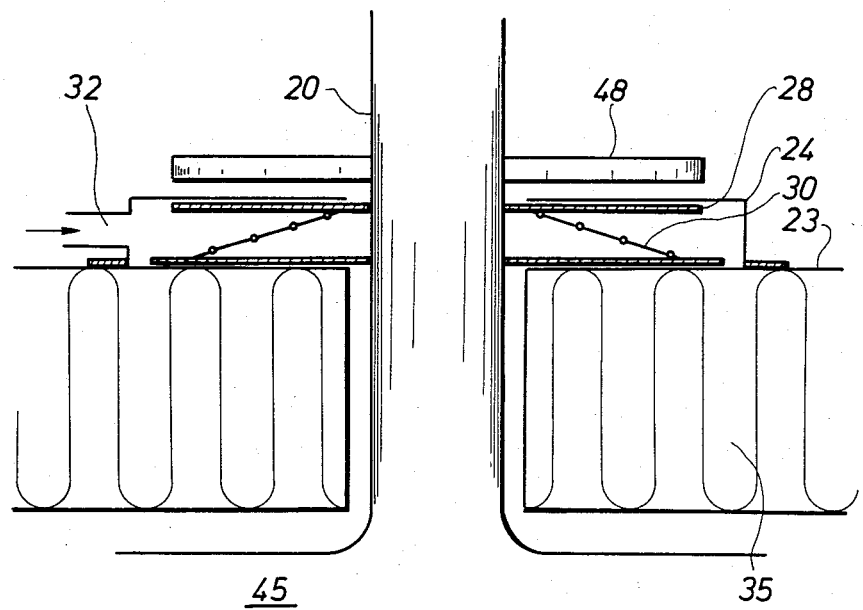

The invention will be described below with reference to the accompanying drawing, in which FIG. 1 illustrates an embodiment of a sterilizing oven with a shaft seal according to the invention, FIG. 2 is a vertical, sectional view through the oven of FIG. 1 taken along the line X—X, and FIG. 3 illustrates an embodiment of a shaft seal according to the invention.

FIG. 1 illustrates a sterilizing oven, and FIG. 2 is a vertical sectional view through the oven taken along the line X—X. The articles to be sterilized are situated in the oven chamber 40. A circulator 45 driven by a motor 50 makes the air circulate, said air being sucked through a channel in one side of the oven from the oven chamber 40 and upwards to the circulator and subsequently pressed into the opposite side of the oven and forced through a tight filter. In FIG. 1 this filter is situated in the left side of the oven, and from said filter the air re-enters the oven chamber 40 in such a manner that the circuit is closed. The same air circulates in the oven. Adjacent the circulator 45, a heating surface not shown and a cooling surface are situated, e.g. an electrically heated heating coil and a water cooled tube coil permitting an adjustment of the temperature of the circulating air. Since the circulating air has and must have a very low content of particles due to the filtration, it is essential that the oven is very tight. The oven is usually situated in a partition between an "impure" and a "pure" chamber. Therefore the oven comprises a door 37 to the impure chamber, and a second door 38 opposing said door 37 and opening on to the pure chamber. The two doors cannot be opened and must not be opened simultaneously. The doors are sealed by double sealing strips 39.

FIG. 3 illustrates an embodiment of a shaft seal according to the invention. A shaft 20 extends through an oven shell 23. At one end the shaft is connected to the circulator of the oven and at the opposite end it is connected to a motor 50, cf. FIG. 2, usually situated immediately oppositely. Below the motor, a cooling disc 48 is provided which ensures the motor against overheating. A circular plate portion 24 pressed outwards and the plate wall 35 of the oven shell form together a sealing chamber 22, cf. FIG. 2, about the shaft 20. The plate portion 24 is screwed fixedly onto the oven shell 23. The connection is sealed by a packing. The shaft 20 is loosely packed with two spring-loaded teflon gaskets 28 partly sealing between the shaft 20 and the sealing chamber 22, cf. FIG. 2. The two teflon gaskets are made in such a manner that by the mounting they fit tightly to the shaft, but upon operation for a short period, a minimum slip exists which then may cause oozing in of impurities. The risk of oozing in is increased by the fact that the circulator usually produces a low pressure exactly at the shaft. In order to avoid penetration of impurities along the shaft, the sealing chamber 22 is provided with a nozzle 32, through which carefully filtered air is fed at a low pressure corresponding to a water column of about 5 mm. The filtered air is fed from a pump 34 through a filter 42, cf. FIG. 1. All the extra parts such as pump, filter, driving motor, relays controlling the closing of the doors, measuring equipment controlling the air resistance of the filter and consequently the operational activity etc. are as far as possible situated either on top of the oven or at a closed service panel appearing from the left side of the oven in FIG. 1, since it is essential to keep the oven doors and the oven front smooth in order to facilitate the cleaning.

In the illustrated embodiment, the sealing chamber is situated on the outside of the oven shell, but it is within the scope of the invention to situate the chamber in the oven shell or immediately inside said shell.

In the illustrated embodiment, the spring 30 is a compression spring shaped as a cone. The spring may also be shaped as a spiral spring. According to a second embodiment of the invention, the spring-loaded gaskets may be situated outside the sealing chamber and be retracted towards the walls of the sealing chamber by a tension spring. According to an additional embodiment, the influence of the spring may be produced by two compression springs situated outside the sealing chamber. According to a fourth embodiment, the gaskets may be situated within the sealing chamber and be pulled out towards the walls of the sealing chamber by means of tension springs.

I claim:

1. In an oven for connectively separating two otherwise independent, isolated medium chambers, seal means for a seal about a rotatable shaft extending through an opening in a wall of the oven, said seal means comprising means forming a chamber surrounding a portion of the shaft and located at the lead-in of the shaft through the oven wall and including a pair of opposed walls extending parallel to the oven wall through which the shaft extends;

a pair of displaceable gaskets surrounding the shaft adjacent the opposed walls of said chamber, said gaskets having only a slip-fit on the shaft and said shaft after rotation is begun having no physical contact with the oven wall, the means forming the chamber and the displaceable gaskets, thus avoiding the creation of wear particles;

spring means urging the pair of gaskets to abut the opposed walls of the chamber to provide sealing cooperation with said walls; and means communicating with said chamber providing pressure above atmospheric pressure within said chamber, creating a positive pressure therein to overcome the low pressure area that normally surrounds the shaft while the shaft rotates and to avoid penetration of impurities along the shaft from either side of said chamber surrounding the shaft, whereby the atmosphere on one side of said chamber does not extend through and mix with the atmosphere on the other side thereof.

2. Seal means in accordance with claim 1 whereby said gaskets are made of teflon.

3. Seal means according to claim 1 wherein said means for providing increased pressure in said chamber includes a pump and filter, the filter being located such that the pump causes air to first pass through the filter and then into said chamber.

4. Seal means in accordance with claim 3 wherein the pressure corresponds to a water column of about 5 mm.

5. Seal means in accordance with claim 1 wherein said chamber surrounding the shaft is located on the outside of the oven wall through which the shaft extends.

6. Seal means in accordance with claim 1 whereby said chamber surrounding the shaft is located on the inside of the oven wall through which the shaft extends.

7. Seal means in accordance with claim 1 wherein said gaskets are located within the chamber and the spring means urges them apart to abut the inside of the walls of said chamber.

8. Seal means in accordance with claim 7 wherein said gaskets are located on the outside of the sealing chamber and the spring means urges them to abut the outside walls of said chamber.

9. In a sterilizing oven with a sterilizing chamber and an air circulating device including a driving means located outside the sterilizing chamber, a fan assembly inside the sterilizing chamber, and a shaft driven by the drive means passing through the wall of the sterilizing chamber and driving the fan assembly, seal means for a seal about said shaft where said shaft passes through the wall of the sterilizing chamber, said seal means comprising means forming an enclosure surrounding a portion of the shaft and located at the lead-in of the shaft through the chamber wall;

a pair of displaceable gaskets surrounding the shaft within the enclosure, said gaskets having only a slip-fit on the shaft and said shaft after rotation is begun having no physical contact with the means forming said enclosure, the sterilizing chamber wall and the displaceable gaskets, thus avoiding the creation of wear particles;

spring means separating the pair of gaskets on the shaft within the enclosure against the walls thereof, thereby creating sealing cooperation with the enclosure; and means communicating with the enclosure providing pressure above atmospheric pressure within the enclosure, creating a positive pressure within the enclosure to overcome a low pressure area that normally surrounds the shaft while the shaft rotates and to avoid penetration of impurities along the shaft from either side of said enclosure surrounding the shaft, whereby the atmosphere on one side of said enclosure does not extend through and mix with the atmosphere on the other side thereof.

* * * * *

UNITED STATES PATENT AND TRADEMARK OFFICE
CERTIFICATE OF CORRECTION

PATENT NO. : 4,498,678
DATED : February 12, 1985
INVENTOR(S) : VESTERGAARD, Alex D.

It is certified that error appears in the above-identified patent and that said Letters Patent is hereby corrected as shown below:

Face of Patent, Assignee address, "Herley" should be --Herlev--.

Column 5, Line 5, "7" should be --1--.

Signed and Sealed this

Fourth Day of February 1986

[SEAL]

Attest:

DONALD J. QUIGG

Attesting Officer

Commissioner of Patents and Trademarks